United States Patent
Nakahata et al.

(10) Patent No.: US 6,262,331 B1
(45) Date of Patent: *Jul. 17, 2001

(54) ABSORBENT ARTICLE HAVING A TOPSHEET THAT INCLUDES SELECTIVELY OPENABLE AND CLOSABLE OPENINGS

(75) Inventors: Hiroshi Nakahata, Cincinnati; Donald C. Roe, West Chester, both of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/178,142

(22) Filed: Oct. 23, 1998

Related U.S. Application Data (63) Continuation-in-part of application No. 09/092,688, filed on Jun. 5, 1998, now Pat. No. 5,873,868.

(51) Int. Cl.[7] ............................................. A61F 13/15
(52) U.S. Cl. ..................... 604/383; 604/385.1; 604/358
(58) Field of Search .................................. 604/358, 383, 604/385.1

(56) References Cited

U.S. PATENT DOCUMENTS

| | | |
|---|---|---|
| 3,842,838 | 10/1974 | Gellert . |
| 4,036,233 | 7/1977 | Kozak . |
| 4,166,464 | 9/1979 | Korpman . |
| 4,389,211 | 6/1983 | Lenaghan . |
| 4,560,372 | 12/1985 | Pieniak . |
| 4,662,877 | 5/1987 | Williams . |

(List continued on next page.)

FOREIGN PATENT DOCUMENTS

| | | |
|---|---|---|
| 0 382 022 B1 | 8/1990 | (EP) . |
| 0 626 160 | 11/1994 | (EP) . |
| 0 847 738 | 6/1998 | (EP) . |

(List continued on next page.)

*Primary Examiner*—John G. Weiss
*Assistant Examiner*—Dennis Ruhl
(74) *Attorney, Agent, or Firm*—David M. Weirich; Steven W. Miller; Jacobus C. Rasser (57) ABSTRACT

An absorbent article adapted to be worn about the lower torso of a wearer. The article includes a liquid-impervious, flexible backsheet adapted to face outwardly relative to the body a wearer, a liquid-pervious topsheet adapted to face the body of the wearer, and an absorbent core positioned between the backsheet and the topsheet. The topsheet is preferably elastically extensible and includes a plurality of slits or cuts that extend through the topsheet material and that enlarge to define a plurality of openings in the topsheet when it is subjected to tensile forces as it is worn. The openings permit solid and semi-solid bodily exudates to pass through the topsheet to the absorbent core as the diaper is worn. Upon removal of the diaper from the body of the wearer the tensile forces within the topsheet are relaxed, thereby causing the openings in the topsheet to close and substantially conceal from view the bodily exudates that have passed through the topsheet.

35 Claims, 5 Drawing Sheets

U.S. PATENT DOCUMENTS

| | | | | |
|---|---|---|---|---|
| 4,731,066 | * | 3/1988 | Korpman | 604/366 |
| 4,892,536 | | 1/1990 | DesMarais et al. . | |
| 4,968,312 | | 11/1990 | Khan . | |
| 4,990,147 | | 2/1991 | Freeland . | |
| 5,023,124 | | 6/1991 | Kobayashi . | |
| 5,037,416 | | 8/1991 | Allen et al. . | |
| 5,062,840 | | 11/1991 | Holt et al. . | |
| 5,171,236 | | 12/1992 | Dreier et al. . | |
| 5,176,672 | | 1/1993 | Bruemmer et al. . | |
| 5,269,775 | | 12/1993 | Freeland et al. . | |
| 5,304,159 | | 4/1994 | Tanji et al. . | |
| 5,304,160 | | 4/1994 | Igaue et al. . | |
| 5,342,342 | | 8/1994 | Kitaoka . | |
| 5,344,516 | | 9/1994 | Tanji et al. . | |
| 5,366,782 | | 11/1994 | Curro et al. . | |
| 5,368,584 | | 11/1994 | Clear et al. . | |
| 5,397,316 | | 3/1995 | LaVon et al. . | |
| 5,425,726 | | 6/1995 | Shimizu et al. . | |
| 5,429,632 | | 7/1995 | Tanji et al. . | |
| 5,439,459 | | 8/1995 | Tanji et al. . | |
| 5,462,541 | | 10/1995 | Bruemmer et al. . | |
| 5,527,302 | | 6/1996 | Endres et al. . | |
| 5,531,729 | | 7/1996 | Coles et al. . | |
| 5,536,555 | | 7/1996 | Zelazoski et al. . | |
| 5,538,555 | | 7/1996 | Zeilazski et al. | 428/138 |
| 5,624,422 | | 4/1997 | Allen . | |
| 5,643,240 | | 7/1997 | Jackson et al. . | |
| 5,702,378 | | 12/1997 | Widlund et al. . | |
| 5,714,107 | | 2/1998 | Levy et al. . | |
| 5,779,690 | | 7/1998 | Gustafasson et al. . | |
| 5,804,021 | | 9/1998 | Abuto et al. . | |
| 5,817,704 | | 10/1998 | Shiveley et al. . | |
| 5,873,868 | * | 2/1999 | Nakahata | 604/383 |
| 5,919,411 | | 7/1999 | Rezai et al. . | |
| 5,957,906 | | 9/1999 | Roe et al. . | |
| 6,049,915 | | 4/2000 | Malowaniec . | |

FOREIGN PATENT DOCUMENTS

| | | |
|---|---|---|
| 2 022 026 | 11/1991 | (ES) . |
| 2 561 078 | 9/1985 | (FR) . |
| 2 302 811 | 2/1997 | (GB) . |
| 3-202057 | 9/1991 | (JP) . |
| 2559050 | 1/1998 | (JP) . |
| WO 93/25172 | 12/1993 | (WO) . |
| WO 95/16417 | 6/1995 | (WO) . |
| WO 95/16418 | 6/1995 | (WO) . |
| WO 95/16419 | 6/1995 | (WO) . |
| WO 95/17867 | 7/1995 | (WO) . |
| WO 95/25493 | 9/1995 | (WO) . |
| WO 96/23466 | 8/1996 | (WO) . |
| WO 96/23467 | 8/1996 | (WO) . |
| WO 97/14385 | 4/1997 | (WO) . |
| WO 97/22319 | 6/1997 | (WO) . |
| WO 97/49366 | 12/1997 | (WO) . |
| WO 98/08476 | 3/1998 | (WO) . |
| WO 98/16180 | 4/1998 | (WO) . |

\* cited by examiner

ABSORBENT ARTICLE HAVING A TOPSHEET THAT INCLUDES SELECTIVELY OPENABLE AND CLOSABLE OPENINGS

This application is a continuation-in-part of Ser. No. 09/092,688, filed Jun. 5, 1998, now U.S. Pat. No. 5,873,868.

FIELD OF THE INVENTION

The present invention relates to disposable absorbent articles, such as disposable diapers. More particularly, the present invention relates to a disposable absorbent article that has a body-facing, extensible topsheet that includes slits that open when the topsheet is subjected to tensile forces and that close when the tensile forces are released.

BACKGROUND OF THE INVENTION

Infants and other incontinent individuals wear absorbent articles such as diapers and incontinent briefs to receive and contain discharged urine and other body exudates. Such absorbent articles function both to contain the discharged materials and to isolate those materials from the body of the wearer and from the wearer's garments and bed clothing. Disposable absorbent articles having many different basic designs are known in the art. For example, U.S. Reissue Pat. No. Re. 26,152, entitled "Disposable Diaper," which issued on Jan. 31, 1967, to Duncan et al., describes a basic disposable diaper structure that has achieved wide acceptance and considerable commercial success.

Disposable absorbent articles that include a topsheet having a single, relatively large area aperture to permit fecal material to pass therethrough are known. Such structures are directed to isolating the fecal material from the body of the wearer. Examples of such known structures are disclosed in U.S. Pat. No. 5,037,416, entitled "Disposable Absorbent Article Having Elastically Extensible Topsheet," which issued on Aug. 6, 1991, to Allen et al.; U.S. Pat. No. 5,269,775, entitled "Trisection Topsheets for Disposable Absorbent Articles and Disposable Absorbent Articles Having Such Trisection Topsheets," which issued on Dec. 14, 1993, to Freeland et al.; and U.S. Pat. No. 5,624,422, entitled "Absorbent Article Having an Extendible Split Core," which issued on Apr. 29, 1997, to Allen.

In addition to isolating fecal material from the body of the wearer, it is also highly desirable that fecal material be concealed from view upon removal of the absorbent article from the body of the wearer. Such concealment is especially desirable when the fecal material is in semi-solid or fluid form, which is typical of bowel movements of newborn and very young infants, and of others suffering from diarrhea. Accordingly, it is an aspect of the present invention to provide a disposable absorbent article that is so configured as to block from view as much as possible of semi-solid and fluid fecal material that is received in article during use.

SUMMARY OF THE INVENTION

Briefly stated, in accordance with one aspect of the present invention, there is provided an absorbent article that is worn about the waist and lower torso. The article includes a liquid impervious backsheet having an outer, garment-facing surface and an inner, body-facing surface. An absorbent core is provided adjacent the body-facing surface of the backsheet. The absorbent core has a shape to enable the core to be placed adjacent the crotch area of the body of a wearer and has the capacity to absorb liquids. A flexible, liquid-impervious topsheet overlies the absorbent core, the topsheet including a plurality of spaced discontinuities that are substantially closed when the topsheet is in an untensioned condition and that are open to define a plurality of spaced openings extending through the topsheet when the topsheet is subjected to tension, to enable solid and semi-solid fecal materials to pass through the topsheet to the absorbent core. Upon removal of the article form the wearer the topsheet openings close to substantially conceal the fecal material.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like.

Figure 1:
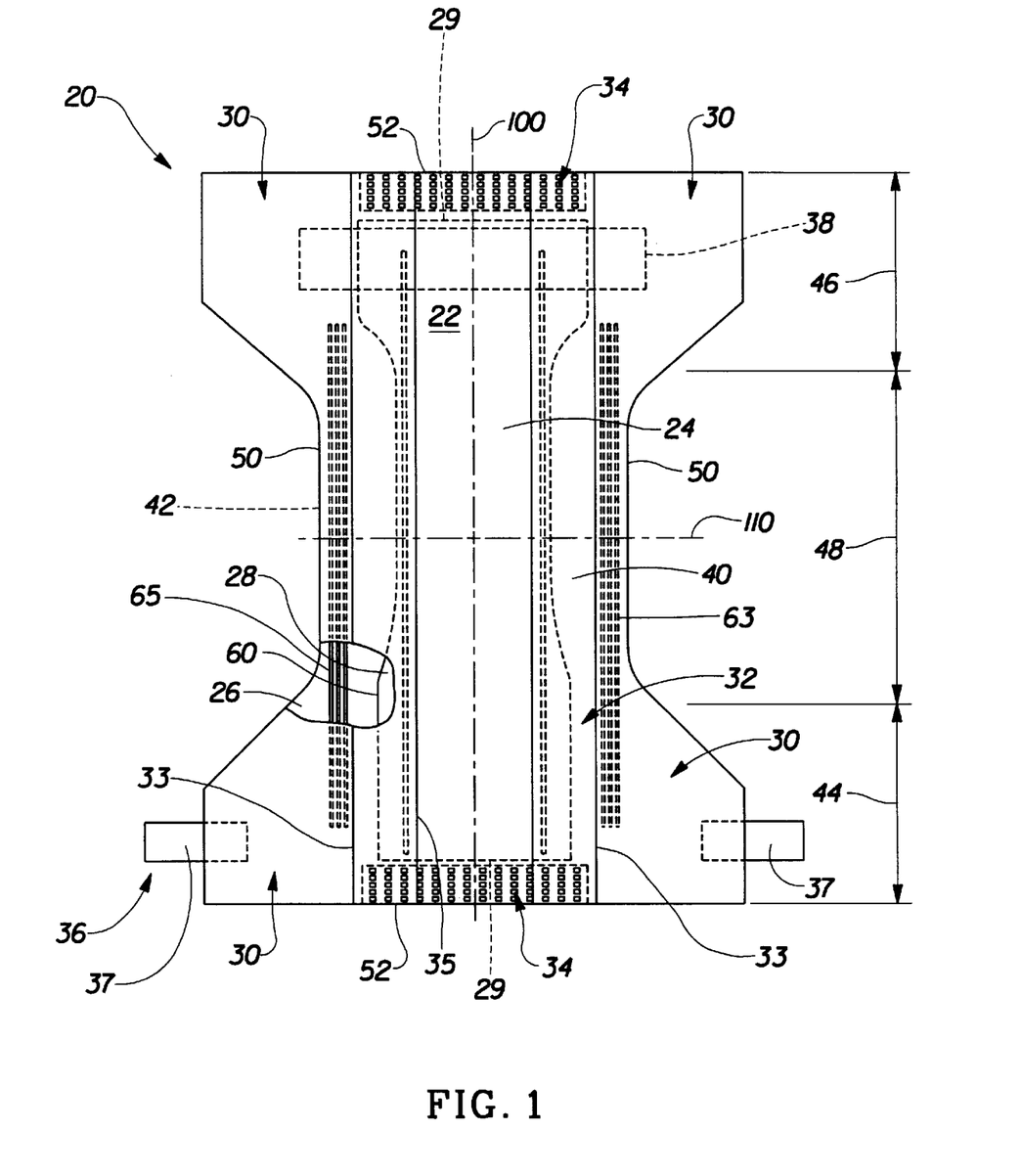
FIG. 1 is a plan view of an absorbent article in accordance with the present invention, in the form of a disposable diaper, having a portion of the structure cut away to reveal underlying structure.

FIG. 1 is a plan view of the diaper 20 of the present invention in a flat-out, state with portions of the structure being cut-away to more clearly show the construction of the diaper 20. The portion of the diaper 20 that faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 36. Diaper 20 is shown in FIG. 1 to have a first waist region 46, a second waist region 44 opposed to the first waist region 46 and a crotch region 48 located between the first waist region and the second waist region. The periphery of the diaper 20 is defined by the outer edges of the diaper 20 in which the longitudinal side edges 50 run generally parallel to the longitudinal centerline 100 of the diaper 20 and the end edges 52 run between the longitudinal side edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. Chassis 22 includes an inner, body-facing surface 40 and an outer, garment-facing surface 42. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the diaper 20 positioned adjacent the garment-facing surface of the absorbent core 28. Backsheet 26 prevents the exudates absorbed and contained therein from soiling articles that may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. Preferably, of the regions is configured so that it will exhibit resistive forces in response to an applied axial elongation in a direction parallel to the predetermined axis before a substantial portion of the other region develops significant resistive forces to the applied elongation. At least one of the regions has a surface-path length that is greater than that of the other region as measured substantially parallel to the predetermined axis while the material is in an untensioned condition. The region exhibiting the longer surface-path length includes one or more deformations that extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-path length to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28, or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Adhesives that have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body-facing surface of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, at least a portion of the topsheet 24 is liquid pervious, permitting liquid to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheet include fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 24 can be made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Proctor & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991, and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein. Alternatively, the topsheet 24 may include an apertured web or film that is hydrophobic. This may be accomplished eliminating the hydrophilizing treatment step from the production process and/or applying a hydrophobic treatment to the topsheet 24, such as a polytetrafluoroethylene compound like SCOTCHGUARD or a hydrophobic lotion composition, as described below. In such embodiments, it is preferred that the apertures be large enough to allow the penetration of aqueous fluids like urine without significant resistance.

Any portion of the absorbent article such as the topsheet 24, the leg cuffs and/or the waist feature may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No.

5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material that is generally compressible, conformable, non-irritating to the wearer's skin, and capable of absorbing and retaining liquids such as urine and other certain body exudates. The absorbent core 28 has longitudinal side edges 60 and end edges 29 and can be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In any case all or a portion of the core may include slits which allow the core to form openings when stretched into which fecal mater can flow.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also include a storage element 152. The storage element may be any material or structure capable of storing bodily exudates. Thus, the storage element 152 may include a single material or a number of materials operatively associated with each other. Further, the storage element 152 may be integral with another element of the diaper 20 or may be one or more separate elements joined directly or indirectly with one or more elements of the diaper 20. Further, the storage element 152 may include a structure that is separate from the core 28 or may include or be part of at least a portion of the core 28.

Suitable materials for use as the storage element 152 may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and more specifically, having pores greater than about 1.0 mm in diameter.) One embodiment of a storage element includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent storage elements are described in European Patent Application No. EP 0 847 738 A1 entitled "Disposable Absorbent Article Having Capacity to Store Low-Viscosity Fecal Material" published Jun. 17, 1998 in the name of Roe, which is hereby incorporated by reference herein. Further, the storage element 152, or any portion thereof, may include or be coated with a lotion or other known substances to add, enhance or change the performance or other characteristics of the element.

Figure 12:
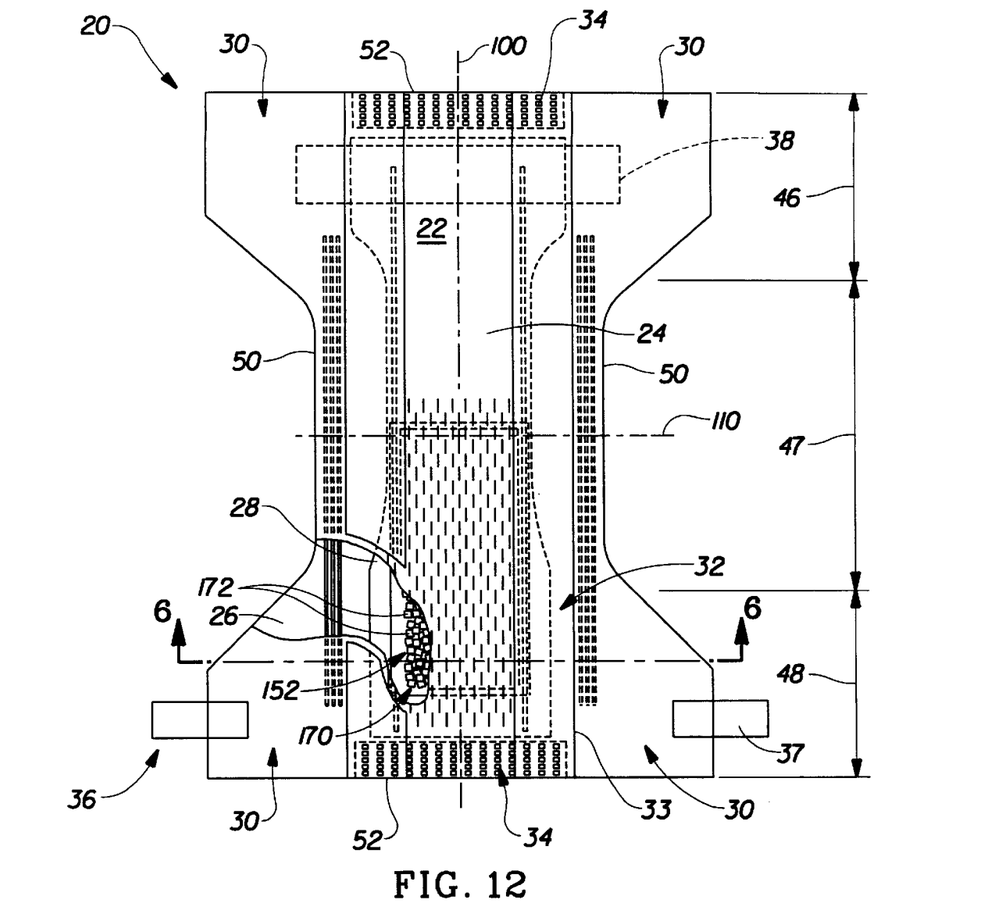
FIG. 12 is a plan view of an absorbent article in accordance with the present invention, in the form of a disposable diaper, having a portion of the structure cut away to reveal underlying structure.
Figure 13:
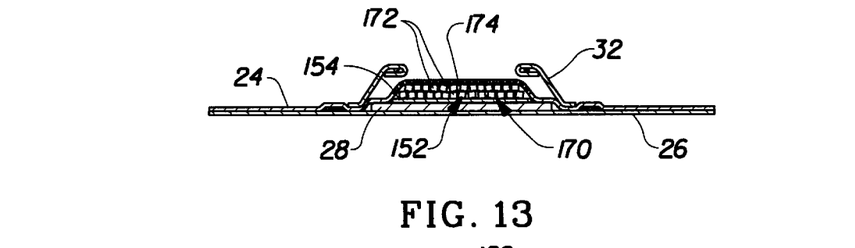
FIG. 13 is an exploded, cross-sectional view of the article of FIG. 12 taken along the line 6—6 thereof.
Figure 14:
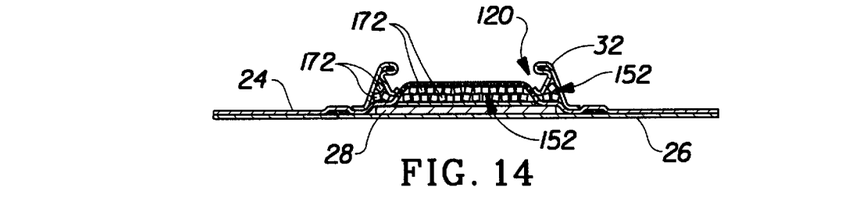
FIG. 14 is an exploded, cross-sectional view of the an alternative embodiment of an article of the present invention.

An alternate embodiment of a storage element 152 includes a macro-particulate structure 170 comprising a multiplicity of discrete particles 172, nonlimiting examples of which are shown in FIGS. 12–14. The macro particles 172 preferably have a nominal size, preferably between about 1.0 mm and about 25.4 mm, and more preferably between about 2 mm and about 16 mm. However, particles as small as 0.5 mm and smaller, and particles larger than about 25.4 mm are contemplated. Particles having a nominal size of about 1.0 mm or greater are those which are generally retained on the surface of a U.S. Standard No. 18 mesh sieve screen. Particles having a nominal size of less than about 25.4 mm are those which generally pass through a U.S. Standard 25.4 mm sieve screen. Particles having a nominal size of 16 mm or greater are those which are generally retained on the surface of a U.S. Standard No. 16 mm sieve screen. The nominal particle size is measured prior to incorporating the particles into a storage element 152 for testing or use. Particles having a nominal size of 8 mm or greater are those which are generally retained on the surface of a U.S. Standard 8 mm sieve screen.

The macro-particulate structure 170 may include any number of particles 172. Further, the particles 172 may be unjoined and free to move within the structure 170 or may be joined to each other by any known means. Alternatively, the structure 170 may include an external support, such as a meltblown hot-melt glue, a web, a netting, a scrim, a thread or other adhesive or nonadhesive entangling supports. Any of the particles 172 may also be joined with any other portion of the diaper structure, such as the topsheet or the core. The particles 172 may also be constrained in patterned, three-dimensional regions such as pleats, "pillows", and pockets.

The individual particles 172 may be made from any material suitable for use in absorbent articles, including the materials described above with regard to the absorbent core 28 or the storage element 152. The materials used in the particles 172 may be absorbent, nonabsorbent, microporous, macroporous, resilient, nonresilient, etc. or may have any other desirable characteristic. Examples of macroporous absorbent materials suitable for use in the particles 172 include highloft nonwovens, open cell foams, bundles of fibers, sponges and the like. Other absorbent materials include cellulosic batts, capillary channel fibers, osmotic storage materials such as superabsorbent polymers, etc. Nonabsorbent particles 172 may comprise plastic, metal, ceramic, glass, closed cell foams, column packing materials, synthetic fibers, gels, encapsulated gas, liquids and the like. Further, any or all of the particles 172 may include odor absorbents, lotions, skin care formulations, antimicrobials, pH buffers, enzyme inhibitors, and the like.

The storage element 152 may comprise a single type of particle 172 (size, shape, material, etc.) or may include a mixture of different particles 172. The mixture may be homogeneous; heterogeneous, as when particles 172 having different properties are disposed in certain areas of the storage element 152; layered; or any other desirable configuration. In some embodiments, more than one type of mixture may be employed (e.g., macroporous and nonabsorbent particles 172 may be homogeneously mixed in one layer while another layer includes only absorbent particles.) Different layers of particles may be directly adjacent each other or may be separated by one or more materials, such as netting, scrim, nonwoven or woven webs, film, foam, adhesive, and the like.

The macro-particulate structure 170 preferably includes a continuous interstitial void space 174 that is defined by the space between the particles 172. By varying the size and/or shape of the particles 172, the interstitial void space 174 can be controlled. The particles may be of any known shape, including spheres, oblate spheroids, rectangular and polygonal solids, and the like. Table I shows the void fractions of particles having particular alternative shapes and nominal sizes. Other suitable shapes and void fractions are described in Perry's Chemical Engineering Handbook, 6th ed., McGraw-Hill, 1984, at p. 18–20.

TABLE I

| Packing Type | Nominal Size (mm) | Void Fraction |
| --- | --- | --- |
| Berl saddles | 6 | 0.60 |
|  | 13 | 0.62 |
| Intalox saddles | 6 | 0.75 |
|  | 13 | 0.78 |
| Pall rings | 16 | 0.87–0.92 |
| Raschig rings | 6 | 0.62 |
|  | 13 | 0.64 |
|  | 19 | 0.72 |

Regardless of the makeup of the storage element 152, it should resist compression so as to maintain some significant level of capacity when a compressive force is applied to the storage element 152. This attribute not only provides capacity within the storage member, but also permits the storage member to act as a spacer or spacing member for spacing apart at least a portion of the topsheet and the absorbent core.) Preferably, the storage element 152 is able to maintain at least about 35% of its original thickness when a compressive force of 1 psi is applied to the structure. More preferably, the storage element 152 should be able to maintain at least about 50%, and most preferably at least about 70% of its original thickness when a compressive force of 1 psi is applied. Generally, in preferred embodiments, the storage element 152 is able to maintain between about 35% and 99% of its original thickness when a compressive force of 1 psi is applied to the structure. More preferably, the storage element 152 should be able to maintain between about 50% and 95% of its original thickness when a compressive force of 1 psi is applied. The storage element 152 should also be capable of restoring itself to substantially its original thickness when the force is removed. Preferably, the storage element 152 should recover at least about 80% of its original thickness, and more preferably at least about 90% of its original thickness after the compression force of 1 psi is removed.

In addition to its storage function, the storage element 152 may transport viscous fluid bodily waste within the absorbent article 20 in directions generally parallel to the plane of the backsheet 26. The transport may be active, such that capillary or other forces result in the movement of the viscous fluid bodily waste or components thereof (e.g., free water). In other embodiments, the transport may be passive whereby viscous fluid bodily waste or components thereof move through the structure under the influence of externally applied forces, such as gravity, wearer pressure or wearer motion. In the case of passive transport, the storage element 152 should have relatively large, interconnected channels, or the like, such that the viscous fluid bodily waste may readily move through the structure with minimum energy input.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 29 of the absorbent core 28 and generally forms at least a portion of the end edge 52 of the diaper 20. Disposable diapers are often constructed so as to have two elastic waist features, one positioned in the first waist region 46 and one positioned in the second waist region 44. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5, 151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 36. The fastening system 36 preferably maintains the side panels 30 of the first waist region 46 and the second waist region 44 in at least partially overlapped condition to provide lateral tensions about the circumference of the diaper 20 when it is worn, to hold the diaper 20 on the wearer. The fastening system 36 preferably comprises securement members 37 that can be in the form of tape tabs that engage a landing member 38, and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. Each of these patents is incorporated herein by reference. In alternative embodiments, opposing sides of the garment may be seamed or welded to form a pant. This allows the article to be used as a pull-on type diaper, such as a training pant.

The diaper 20 may also comprise side panels 30. The side panels 30 may be elastic or extensible to provide a more comfortable and body-conforming fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear.

While the diaper 20 of the present invention preferably has the side panels 30 disposed in the second waist region 44, the diaper 20 may be provided with side panels 30 disposed in the first waist region 46 or in both the first waist region 46 and the second waist region 44. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151, 092 issued to Buell on Sep. 9, 1992; and U.S. Pat. No. 5, 221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

The diaper 20 preferably further includes leg cuffs 32 that provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above. In addition to leg cuffs 32, diaper 20 can also include an elastic gasketing cuff 63 with one or more elastic strands 65 positioned outboard of the barrier cuff.

Embodiments of the present invention may also include pockets for receiving and containing waste, spacers or spacing members which provide voids for waste, barriers for limiting the movement of waste within the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. The disclosures of each of the above-cited patents and publications are hereby incorporated by reference herein.

In addition to being liquid permeable the topsheet is preferably extensible, either inelastically or elastically. The attribute of liquid permeability is generally preferred in a topsheet, whether it is in its extended state or in its relaxed or contracted state, in order to enable liquids to pass therethrough to be absorbed by absorbent core 28. Elastic extensibility can be provided to the topsheet by forming the topsheet from an inherently elastic material, such as a thin, apertured sheet made from rubber, latex, elastically extensible polymeric film, or the like. Additionally, the topsheet can be formed from an inherently substantially inelastic material, such as a woven or nonwoven sheet of fibrous material that is so formed or so treated as to be made to be elastic, such as by means of corrugating, ring rolling, or the like (see description and patents incorporated by reference in the discussion above relating to elastic extensibility of backsheet 26). If elastic extensibility is provided to the topsheet by one of the rolling techniques identified hereinabove, it is preferred that the attribute of elastic extensibility be provided in at least the cross-machine direction, so that at least a portion of the topsheet can be extended in a transverse direction relative to diaper 20, which corresponds with the width dimension of the topsheet and of the diaper.

A topsheet in accordance with the present invention preferably includes one or more regions that when placed under tension includes a plurality of relatively small openings that extend through the topsheet. Such openings permit the passage through the topsheet of semi-solids, such as loose or runny bowel movements of the character typically associated with newborn infants and very young babies, and of others suffering from diarrhea. When the tensile forces acting on such a topsheet are released, the elasticity of the material causes the topsheet to contract to its original, untensioned condition, resulting in the closing of the previously-existing small openings, thereby preventing the further passage through the topsheet of non-liquids. Upon the closing of the openings the matter that has passed through the topsheet is retained between the absorbent core and the topsheet. Moreover, if the topsheet material is opaque, or substantially opaque, the bowel movement will not be visible, thereby rendering diapering a less unappealing and less unwelcome chore.

Regions of the topsheet that are intended to present openings through the topsheet when the topsheet is placed under laterally-directed tensile forces are preferably pierced by providing a plurality of discontinuities in the form of slits, cuts, or perforations that extend through the topsheet. The discontinuities are arranged to define in the topsheet a predetermined pattern of discrete, localized regions of slits, cuts, or perforations. The discontinuities permit the edges of the topsheet that surround the discontinuities to separate from each other and thereby provide the desired plurality of small openings. Such discontinuities are preferably in the form of rectilinear cuts, curvilinear cuts, or combinations thereof, that can be made by a variety of cutting devices of the types known to those skilled in the art.

Figure 2:
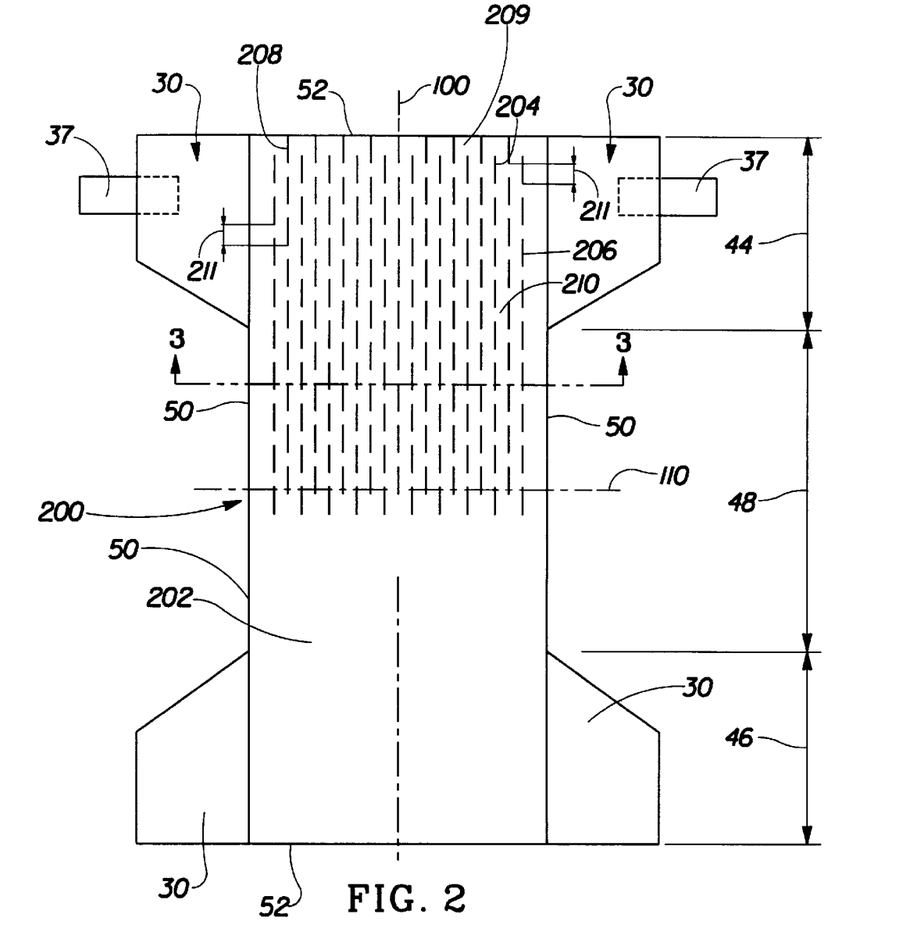
FIG. 2 is a view similar to that of FIG. 1, showing an absorbent article in accordance with the present invention with the article in untensioned condition before application to the body of a wearer.

Referring now to FIG. 2, there is shown the body-facing surface of a disposable diaper 200 having a topsheet 202 in accordance with the present invention. In all other respects the structure of diaper 200 is the same as that shown in FIG. 1 and described above in connection with diaper 20. As shown in FIG. 2, topsheet 202 includes a pattern 204 of discrete, spaced discontinuities defined by a plurality of rectilinear cuts or slits 206 that extend through topsheet 202. Slits 206 are preferably oriented so that they extend in the longitudinal direction of diaper 200, in the direction of longitudinal centerline 100, and they also are preferably aligned to define a plurality of laterally spaced columns 208 that also extend in the longitudinal direction of diaper 200. As they are shown in FIG. 2, slits 206 are of substantially equal length, but they can be of different lengths, if desired. Also as shown in FIG. 2, slits 206 of a given column 208 are longitudinally and equally spaced from each other, and adjacent columns 208 are at a transverse spacing 209 from each other and are positioned so that the ends of slits 206 of one column 208 are longitudinally offset from the ends of slits 206 of adjacent columns 208. Accordingly, laterally opposite the intervening uncut spaces between aligned slits 206 of one column 208 are slits 206 of the adjacent columns 208. As it is illustrated in FIG. 2, topsheet 202 is in its relaxed, untensioned condition, at a time when slits 206 are in substantially closed condition in that the edges of the slits are substantially in contact with each other so as to make topsheet 202 appear to the naked eye to be a continuous topsheet without cuts or slits, but still liquid permeable.

Figure 3:
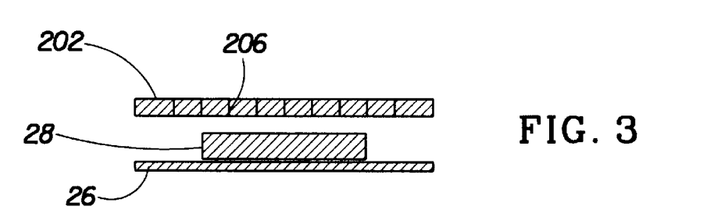
FIG. 3 is an exploded, cross-sectional view of the article of FIG. 2 taken along the line 3—3 thereof.
Figure 4:
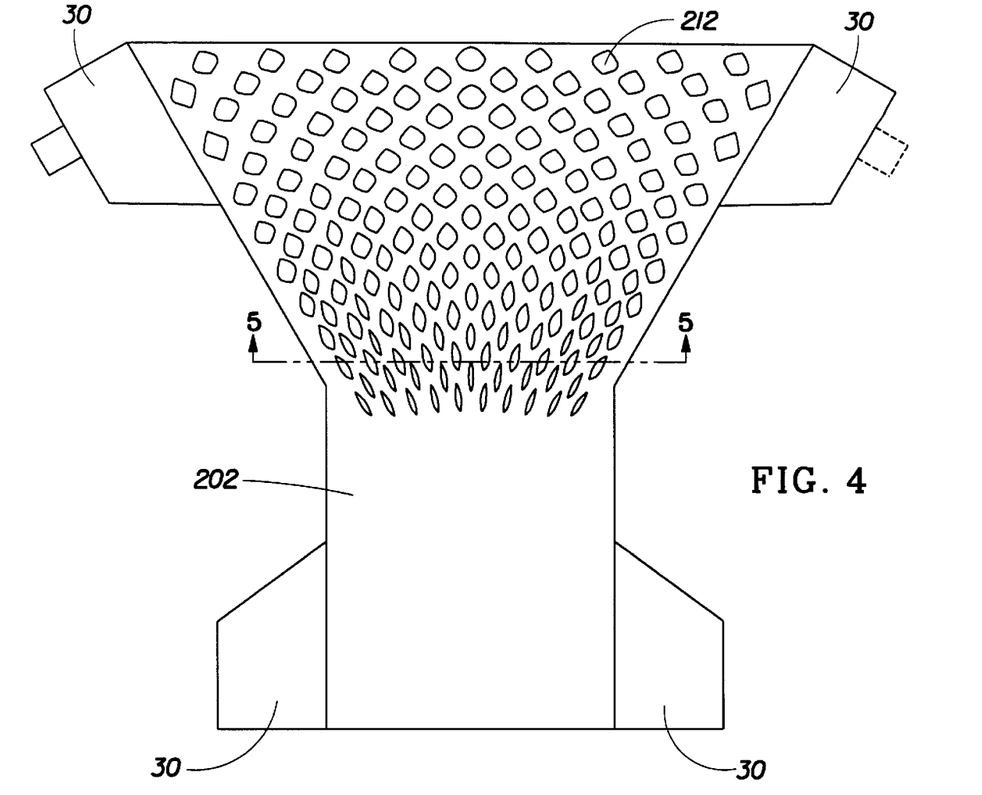
FIG. 4 is a view similar to that of FIG. 2, showing a portion of the absorbent article subjected to tension in the lateral direction.
Figure 5:
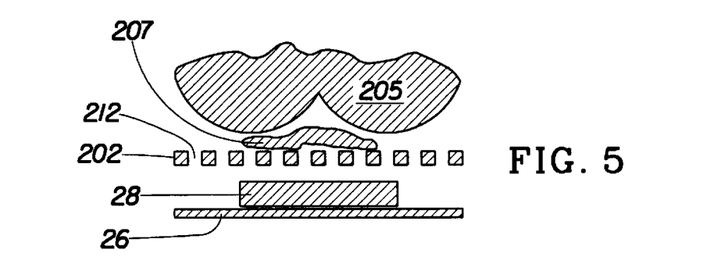
FIG. 5 is an exploded, cross-sectional view of the article of FIG. 4 taken along the line 5—5 thereof.
Figure 6:
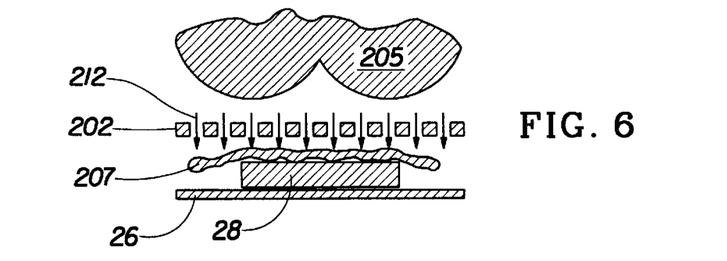
FIG. 6 is a view similar to that of FIG. 5 showing fecal material that has passed through openings in the topsheet of the article.

When laterally-directed tensile forces are applied to topsheet 202, the extensibility of topsheet 202 results in lateral stretching of the topsheet. Under that condition, the uncut areas 210 between adjacent slits 206 are subjected to the laterally-directed tensile forces and they stretch in a lateral direction, causing edges of slits 206 to separate from each other to provide individual openings 212, as shown in FIG. 3. Because of the disposition, size, and spacing of slits 206 relative to each other, openings 212 are diamond-shaped, as shown in FIG. 4. Such laterally-applied tensile forces are imposed when ears 30 in rear waist region 44 of diaper 200 are each drawn laterally outwardly in opposite directions, to enable the diaper rear waist region to be drawn against the back of the wearer and around the wearer's waist so that ears 30 of rear waist area 44 at least partially overlap ears 30 of front waist region 46. When in the condition illustrated in FIG. 4, the plural openings 212 in tensioned topsheet 202 are sufficiently large to permit semisolid fecal matter 207 to pass from wearer 205 through openings 212 in topsheet 202 to absorbent core 28, as shown in FIG. 5. When the passage of fecal material 207 occurs through topsheet 202, the liquid component of the material is absorbed by absorbent core 28 while the solid component of the material remains between absorbent core 28 and topsheet 202, as shown in FIG. 6.

Figure 7:
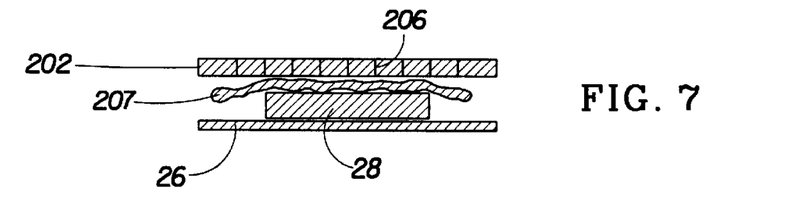
FIG. 7 is a view similar to that of FIG. 6 but showing the article after the openings in the topsheet have closed.

When diaper 202 is subsequently removed from the body of the wearer, the tensile forces that previously served to hold the diaper snugly about the waist of the wearer are released, thereby permitting topsheet 202 to return to its original, untensioned condition. Upon release of the tensile forces acting on topsheet 202, and the contraction of topsheet 202 to its original, unstretched condition, the plurality of small openings 212 that were present when topsheet 202 was in the tensioned state are now closed, as illustrated in FIG. 7, which serves to conceal from view the portion of the fecal material that passed through the topsheet.

Additionally or alternatively, the topsheet 202 may be subjected to longitudinal-directed tensile forces. In such cases, the longitudinal extension of the topsheet cause the edges of slits 206 to separate from each other to provide individual openings 212, as described above. Such longitudinally-applied tensile forces may be imposed when the first waist region 46 and the second waist region 44 are drawn longitudinally apart during the diapering process.

Also, if the diaper 20 is configured such that the topsheet 202 is shorter longitudinally than the backsheet 26, the topsheet 202 will be expanded when the diaper is fitted to a wearer, thereby opening the slits 206.

When slits 206 in topsheet 202 are of rectilinear form, as shown in FIG. 2, the slits 206 can have a length of from about 1.0 mm to about 100 mm, preferably from about 2.0 mm to about 50.0 mm, and most preferably from about 3.0 mm to about 10.0 mm. The longitudinal spacing 210 between adjacent slits 206 can be up to about 10.0 mm, preferably up to about 5.0 mm, and most preferably up to about 2.0 mm. The transverse spacing 209 between adjacent columns 208 of aligned slits 206 can be up to about 10.0 mm, preferably up to about 5.0 mm, and most preferably up to about 2.0 mm. The longitudinal offset 211 of the ends of the slits 206 in adjacent columns 208 can be from about 0 mm to about 100 mm, preferably from about 2.0 mm to about 50 mm, and most preferably from about 3.0 mm to about 10.0 mm.

Although shown in FIG. 2 as a series of parallel columns 208 of aligned slits 206, slit pattern 204 can, if desired, be such that the slits of a given column are not precisely aligned with each other but are laterally offset from each other, staggered or randomly disposed throughout all or a portion of the topsheet. Preferably, however, slits 206 are so disposed that the application of tensile forces to topsheet 202 results in a plurality of substantially equal area openings having an area of from about 1.0 mm$^2$ to about 2500 mm$^2$, that are substantially uniformly distributed over the entirety of cut pattern 204. Although openings 212 preferably are of substantially equal area, the areas of the openings need not be equal. For example, the areas of openings 212 can be larger in the portion of topsheet 202 that lies at and adjacent longitudinal centerline 100 of diaper 200. Additionally, larger openings 212 can be provided in the portion of topsheet 202 that lies at and adjacent the intersection of longitudinal centerline 100 and transverse centerline 110.

Figure 8:
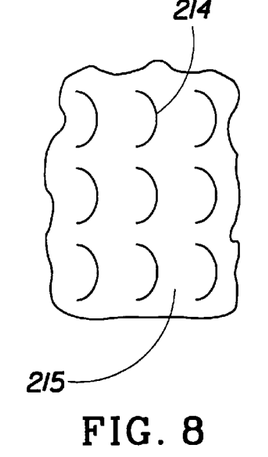
FIG. 8 is a fragmentary plan view of a portion of a topsheet including curvilinear slits.
Figure 9:
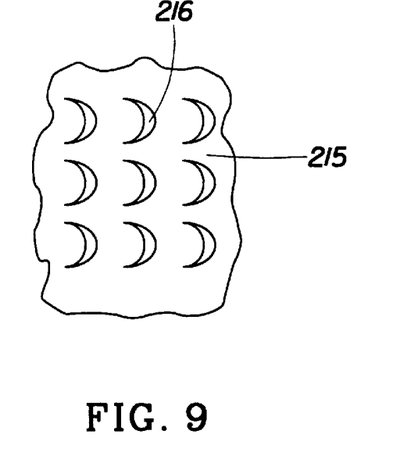
FIG. 9 is a view similar to that of FIG. 8 but showing the topsheet of FIG. 8 when placed under tension.

Although slits 206 are shown in FIG. 2 as having a rectilinear form, they can alternatively be curvilinear or of any other suitable geometry. If desired, or a combination of rectilinear and curvilinear forms. One form of such curvilinear slits 214 is shown in FIG. 8. When a topsheet 215 having the slit form and the column and row slit pattern shown in FIG. 8 is stretched laterally, slits 214 open to define respective substantially crescent-shaped openings 216, as shown in FIG. 9.

Figure 10:
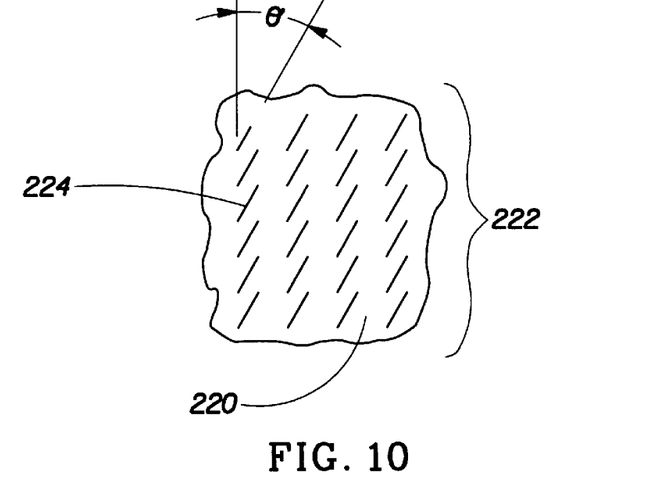
FIG. 10 is a fragmentary plan view of a portion of a topsheet including a plurality of angularly disposed rectilinear slits.

In addition to the longitudinally aligned slits illustrated in slit pattern 204 shown in FIG. 2, the slit pattern can be arranged as shown in FIG. 10. As there shown, the individual slits in topsheet 220 can be disposed in a pattern 222 of angularly disposed slits 224. Although slits 224 are each defined by a straight line cut, and although slit pattern 222 of FIG. 10 defines a series of laterally spaced, longitudinal columns each defined by a plurality of slits 224, each of slits 224 is inclined at an acute angle θ relative to a line 226 that is parallel to the longitudinal axis of the diaper. The inclination angle θ preferably is less than about 45°, and more preferably is less than about 30°. Moreover, slits 224 can each be disposed at the same inclination angle, as shown in FIG. 10, or, alternatively, the inclination angles of the slits can differ within slit pattern 222, to provide topsheet openings that have different areas in different regions of the topsheet. Additionally, the slit pattern can include both rectilinear slits and curvilinear slits, if desired.

Slit pattern 204 shown in FIG. 2 can, if desired, be an overall pattern that extends over the entire surface of topsheet 202. Additionally, however, slit pattern 204 can be provided only in a limited area of topsheet 202, such as in the rear waist region 44 and the crotch region 48, as shown in FIG. 2. Preferably, slit pattern 204 extends over an area sufficiently large that when topsheet 202 is subjected to tension, at least some of the resulting openings in the topsheet are positioned opposite the wearer's anal opening when the diaper is worn, regardless of the position of the diaper relative to the body of the wearer and regardless of the size of the body of the wearer. Accordingly, it is preferred that slit pattern 204 extend over at least a portion of crotch region 48. Of course, that same slit pattern coverage variation also applies to curvilinear slits 214 and angularly disposed slits 224 shown in figures and 10, respectively.

In preferred embodiments, at least a portion of the topsheet preferably has a trans-topsheet capacity when extended of at least about 0.20 g/in$^2$, more preferably at least about 0.60 g/in$^2$. (Trans-topsheet capacity "TTSC", as used herein refers to the amount of fluid which passes through a portion of the topsheet material per unit area when subjected to the test methods described in detail in European Patent Application No. EP 0 847 738 A1 entitled "Disposable Absorbent Article Having Capacity to Store Low-Viscosity Fecal Material" published Jun. 17, 1998 in the name of Roe, which is incorporated by reference herein.) It is also preferred that the topsheet have an effective open area of greater than or equal to about 15%, preferably about 20%. Exemplary topsheets and the methods for measuring the effective open area are described in detail in U.S. Pat. No. 5,342,388 which is hereby incorporated by reference herein.

It is also preferred that backsheet 26 be extensible, preferably having an extensibility of from about 10% to about 500%, more preferably from about 50% to about 300%, so that the backsheet and the topsheet each stretch laterally simultaneously when diaper 200 is applied to the body of a wearer. Such mutual extension of the backsheet and topsheet results in a snug and body-conforming fit of the diaper on the body of the wearer, with the topsheet extended an amount sufficient to open the slits formed therein, and without excessive bagginess or bulkiness of the diaper so that it does not cause undesirable protrusion of the wearer's clothing that is positioned about the wearer's lower torso. Preferably, the extensibility of backsheet 26 is provided in at least the rear waist region 44 and in at least a portion of crotch region 48 of the diaper.

Figure 11:
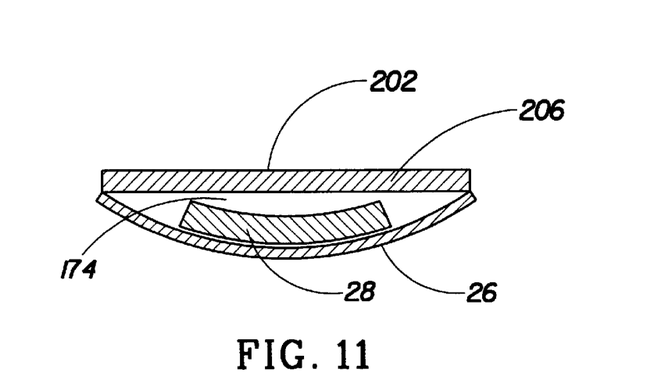
FIG. 11 is a cross-sectional view of another form of absorbent article having a substantially inelastic backsheet that has a greater width than that of an attached elastic topsheet.

Instead of having the attribute of elastic extensibility, backsheet 26 can alternatively be of a substantially inelastic nature, if desired. In that event, it is preferred that backsheet 26 have a greater width and/or length than that of topsheet 202, as shown in FIG. 11, wherein the narrower, slit-containing, elastically extensible topsheet 202 causes a substantially crescent-shaped gap between the topsheet and the absorbent core 28 when the diaper is viewed in cross section. When a diaper having such a structure is applied to the body of a wearer topsheet 202 will be subjected to tension, thereby causing slits 206 provided therein to open and to permit the benefits of the present invention to be realized.

Although particular embodiments of the present invention have been illustrated and described, it would be apparent to those skilled in the art that various other changes and modifications can be made without departing from the spirit of the present invention. It is therefore intended to cover in the appended claims all such changes and modifications that are within the scope of this invention.

What is claimed is:

1. An absorbent article adapted to be worn adjacent the lower torso of a wearer for receiving and retaining bodily exudates, the absorbent article having a pair of longitudinal edges and a pair of end edges, said absorbent article comprising:
   a. a liquid impervious, backsheet having an outer, garment-facing surface and an inner, body-facing surface;
   b. an absorbent core having a shape to enable the core to be placed adjacent the body of a wearer and having the capacity of absorbing liquids;
   c. a flexible, liquid-pervious topsheet overlying the absorbent core, the topsheet including a plurality of spaced discontinuities disposed over at least a portion of the absorbent core, the spaced discontinuities are substantially closed when the topsheet is in an untensioned condition and are open to define a plurality of spaced openings extending through the topsheet when the topsheet is subjected to tension, to enable solid and semi-solid body exudates to pass through the topsheet; and
   d. a storage element disposed between at least a portion of the topsheet and at least a portion of the absorbent core for receiving the bodily exudates.

2. An absorbent article in accordance with claim 1, wherein the article includes a front waist region, a rear waist region, and a crotch region, and wherein the discontinuities are disposed adjacent at least a portion of the storage element.

3. The absorbent article of claim 1 wherein the storage element spaces the topsheet from the absorbent core.

4. The absorbent article of claim 1 further including a spacing member disposed between the topsheet and the backsheet which provides a cavity between at least a portion of the topsheet and the absorbent core for receiving bodily exudates.

5. The absorbent article of claim 1 wherein the backsheet has a length or width greater than the length or width, respectively, of the topsheet such that when the topsheet and the backsheet are joined together a cavity is formed between the topsheet and the storage element.

6. The absorbent article of claim 1, wherein the discontinuities are cuts that extend through the topsheet.

7. The absorbent article of claim 6, wherein at least some of the cuts are rectilinear and/or curvilinear.

8. The absorbent article of claim 6, wherein the cuts are disposed in a plurality of spaced, substantially aligned columns, staggered columns or are generally randomly disposed throughout at least a portion of the topsheet.

9. The absorbent article of claim 1, wherein the topsheet is elastically extensible.

10. The absorbent article of claim 1, wherein the topsheet is inelastically extensible.

11. The absorbent article of claim 1, wherein the backsheet is elastically extensible.

12. The absorbent article of claim 1 wherein the backsheet is substantially inextensible.

13. The absorbent article of claim 1 wherein the article includes a front waist region, a rear waist region, and a crotch region, and wherein the discontinuities are disposed in at least the crotch region of the absorbent article.

14. The absorbent article of claim 1 wherein the storage element includes a material selected from the following group: large cell open foams, macro-porous compression resistant nonwoven highlofts, large size particulate foams of open and closed cell foams, highloft nonwovens, polyolefin, polystyrene, polyurethane foams or particles, structures comprising a multiplicity of vertically oriented looped strands of fibers, and absorbent core structures having punched holes or depressions.

15. The absorbent article of claim 1 wherein at least a portion of the topsheet has an effective open area of greater than or equal to about 15%.

16. The absorbent article of claim 1 wherein the absorbent core is slit such that it can expand to form openings in the core for receiving fecal matter.

17. An absorbent article adapted to be worn adjacent the lower torso of a wearer for receiving and retaining bodily exudates, the absorbent article having a pair of longitudinal edges and a pair of end edges, said absorbent article comprising:
   a. a liquid impervious, backsheet having an outer, garment-facing surface and an inner, body-facing surface;
   b. a flexible, liquid-pervious topsheet overlying an absorbent core, the topsheet including a plurality of spaced discontinuities disposed over at least a portion of the absorbent core, the spaced discontinuities are substantially closed when the topsheet is in an untensioned condition and are open to define a plurality of spaced openings extending through the topsheet when the topsheet is subjected to tension, to enable solid and semi-solid body exudates to pass through the topsheet; and
   d. a storage element disposed between at least a portion of the topsheet and at least a portion of the absorbent core for receiving the bodily exudates, the storage element including a multiplicity of macro-particulate elements.

18. The absorbent article of claim 17 wherein the macro-particulate elements have a nominal size of between about 1.0 mm and about 25.4 mm.

19. The absorbent article of claim 17 wherein at least some of the macro-particulate elements are absorbent.

20. The absorbent article of claim 17 wherein at least some of the macro-particulate elements are non-absorbent.

21. The absorbent article of claim 17 wherein at least some of the macro-particulate elements are microporous.

22. The absorbent article of claim 17 wherein at least some of the macro-particulate elements are resilient.

23. The absorbent article of claim 17 wherein the storage element includes a support associated with at least some of the macro-particulate elements, the support selected from the following group: a glue, a web, a netting, a scrim, a thread.

24. The absorbent article of claim 17 including a mixture of different macro-particulate elements.

25. The absorbent article of claim 17 wherein the storage element includes more than one layer of macro-particulate elements.

26. The absorbent article of claim 17 wherein the storage element has an original thickness measured in the absence of a compressive force and the storage element is capable of maintaining at least about 35% of the original thickness when subjected to a compressive force of 1 psi.

27. The absorbent article of claim 17 wherein the storage element is capable of maintaining at least about 50% of the original thickness when subjected to a compressive force of 1 psi.

28. The absorbent article of claim 17 wherein the backsheet has a length or width greater than the length or width, respectively of the topsheet such that when the topsheet and the backsheet are joined together a cavity is formed between the topsheet and the storage element.

29. The absorbent article of claim 17 further including a spacing member disposed between the topsheet and the backsheet which provides a cavity between at least a portion of the topsheet and the absorbent core for receiving bodily exudates.

30. The absorbent article of claim 17 wherein the storage element spaces the topsheet from the absorbent core.

31. The absorbent article of claim 17 wherein at least a portion of the topsheet has an effective open area of greater than or equal to about 15%.

32. An absorbent article adapted to be worn adjacent the lower torso of a wearer for receiving and retaining bodily exudates, the absorbent article having a pair of longitudinal edges and a pair of end edges, said absorbent article comprising:
- a. a liquid impervious, backsheet having an outer, garment-facing surface and an inner, body-facing surface;
- b. an elastically extensible, liquid-pervious topsheet overlying an absorbent core, the topsheet including a plurality of spaced discontinuities that are substantially closed when the topsheet is in an untensioned condition and that are open to define a plurality of spaced openings extending through the topsheet when the topsheet is subjected to tension, to enable solid and semi-solid body exudates to pass through the topsheet; and
- d. a storage element disposed between at least a portion of the topsheet and at least a portion of the absorbent core for receiving the bodily exudates, the storage element including a multiplicity of macro-particulate elements.

33. The absorbent article of claim 32 wherein the macro-particulate elements have a nominal size of between about 1.0 mm and about 25.4 mm.

34. The absorbent article of claim 32 wherein the storage element includes a support associated with at least some of the macro-particulate elements, the support selected from the following group: a glue, a web, a netting, a scrim, a thread.

35. The absorbent article of claim 32 wherein the backsheet has a length or width greater than the length or width, respectively, of the topsheet such that when the topsheet and the backsheet are joined together a cavity is formed between the topsheet and the storage element.

* * * * *